(12) United States Patent
Kubo et al.

(10) Patent No.: US 8,157,790 B2
(45) Date of Patent: Apr. 17, 2012

(54) POSITION CONFIRMING CATHETER

(75) Inventors: Masaaki Kubo, Suita (JP); Takehiko Saito, Fujinomiya (JP); Takenari Ito, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 346 days.

(21) Appl. No.: 11/430,849

(22) Filed: May 10, 2006

(65) Prior Publication Data

US 2006/0259011 A1 Nov. 16, 2006

(30) Foreign Application Priority Data

May 13, 2005 (JP) ................................ 2005-141434

(51) Int. Cl.
*A61M 25/098* (2006.01)
(52) U.S. Cl. ........................................ 604/529; 604/526
(58) Field of Classification Search .................. 604/264, 604/52–530, 532, 103.1; 600/435; D24/112
See application file for complete search history.

(56) References Cited

U.S. PATENT DOCUMENTS

| | | | | |
|---|---|---|---|---|
| 4,838,879 A | * | 6/1989 | Tanabe et al. ................... | 604/529 |
| 4,922,924 A | * | 5/1990 | Gambale et al. ............... | 600/585 |
| 5,174,302 A | * | 12/1992 | Palmer ........................... | 600/585 |
| 5,540,707 A | * | 7/1996 | Ressemann et al. ........... | 606/159 |
| 5,630,806 A | * | 5/1997 | Inagaki et al. ................. | 604/524 |
| 5,947,940 A | * | 9/1999 | Beisel ............................ | 604/526 |
| 5,951,539 A | | 9/1999 | Nita et al. | |
| 6,152,912 A | | 11/2000 | Jansen et al. | |
| 6,159,187 A | * | 12/2000 | Park et al. ..................... | 604/264 |
| 6,296,631 B2 | * | 10/2001 | Chow ............................. | 604/525 |
| 6,348,041 B1 | * | 2/2002 | Klint ............................. | 600/585 |
| 6,451,005 B1 | * | 9/2002 | Saitou et al. .................. | 604/526 |
| 6,520,934 B1 | | 2/2003 | Lee et al. | |
| 6,638,245 B2 | | 10/2003 | Miller et al. | |
| 6,648,837 B2 | * | 11/2003 | Kato et al. ..................... | 600/585 |
| 7,104,979 B2 | * | 9/2006 | Jansen et al. ................... | 604/525 |
| 2002/0156459 A1 | | 10/2002 | Ye et al. | |
| 2002/0198491 A1 | | 12/2002 | Miller et al. | |
| 2003/0109823 A1 | * | 6/2003 | Hobot et al. ............... | 604/103.1 |

FOREIGN PATENT DOCUMENTS

| | | |
|---|---|---|
| EP | 1 068 876 A2 | 1/2001 |
| EP | 1 457 230 A1 | 9/2004 |
| WO | WO 03/020353 A1 | 3/2003 |

OTHER PUBLICATIONS

Notice of Opposition dated Nov. 23, 2009 issued by European Patent Office in European Patent Application No. 06 00 9537.9.

* cited by examiner

*Primary Examiner* — Kevin C Sirmons
*Assistant Examiner* — Kami A Bosworth
(74) *Attorney, Agent, or Firm* — Buchanan Ingersoll & Rooney PC

(57) ABSTRACT

A catheter includes an inner layer, an outer layer, a reinforcement layer located between the inner layer and the outer layer, and a marker composed of a contrast material for confirming the position of the distal end portion of the catheter from outside the living body. The reinforcement layer is composed of a spiral first filamentous member, with a gap provided between those portions of the first filamentous member which are adjacent to each other along the longitudinal direction of the catheter. The marker is formed by spirally winding a second filamentous member having a filament diameter smaller than the gap, and has a portion in close contact with the inner layer in the gap.

18 Claims, 4 Drawing Sheets

US 8,157,790 B2

POSITION CONFIRMING CATHETER

FIELD OF THE INVENTION

The present invention generally relates to a catheter. More particularly, the invention pertains to a catheter including an inner layer, an outer layer, a reinforcement layer, and a marker composed of a contrast material to permit confirmation of the position of the distal end portion of the catheter from outside a living body.

BACKGROUND DISCUSSION

In recent years, medical treatment has been performed at sites where surgical operations are difficult or which require low invasiveness to the living body, such as PTCA (Percutaneous Transluminal Coronary Angioplasty). In such a treatment, the distal end portion of a catheter is guided to the vicinity of an angiostenosis by use of a guide wire.

One example of a catheter used for such purpose is described in U.S. Pat. No. 5,951,539. The catheter disclosed in this patent includes an inner layer, an outer layer, a reinforcement layer located between the inner layer and the outer layer, and a marker having a contrast property provided at a distal end portion of the catheter. The marker permits confirmation of the position of the distal end portion of the catheter from outside the living body.

However, the catheter possesses a quite large outside diameter due to the sequential lamination of the inner layer, the outer layer, the reinforcement layer, and the marker. It may thus be difficult for the catheter to pass through a target site with a small inside diameter, for example, an angiostenosis or a peripheral portion of a blood vessel. In addition, the width of the band constituting the marker is relatively large to ensure relatively easy confirmation of the position of the distal end portion of the catheter. However, this may spoil or degrade the flexibility of the distal end portion of the catheter.

SUMMARY

According to one aspect, a catheter which is positionable in a living body comprises a catheter body possessing a lumen, wherein the catheter body comprises an inner layer, an outer layer, a marker and a reinforcement layer. The inner layer extends along at least the distal end portion of the catheter body and possesses an inner surface exposed to the lumen of the catheter body. The outer layer contacts the inner layer and extends along at least the distal end portion of the catheter body. The reinforcement layer is positioned between the inner layer and the outer layer, and comprises a first filamentous member. The first filamentous member extends in a spiral manner about the inner layer so that portions of the first filamentous member which are adjacent one another in a longitudinal direction of the catheter body are spaced apart. The marker is comprised of a material possessing contrast properties permitting confirmation of the position of the distal end portion of the catheter from outside the living body. The marker comprises a second filamentous member that extends in a spiral manner about the inner layer. At least a portion of the second filamentous member is positioned between portions of the first filamentous member which are adjacent one another in the longitudinal direction of the catheter body and is in contact with the inner layer. In addition, the marker and the reinforcement layer are covered by the outer layer.

According to another aspect, a catheter comprises an inner layer, an outer layer, a reinforcement layer located between the inner layer and the outer layer, and a marker including a contrast material which permits confirmation of the position of the distal end portion of the catheter from outside the living body. The reinforcement layer includes a spiral first filamentous member, with a gap provided between those portions of the first filamentous member which are adjacent to each other along the longitudinal direction of the catheter. The marker is formed by spirally winding a second filamentous member having a filament diameter smaller than the gap, with a portion of the second filamentous member in contact with the inner layer in the gap.

The marker preferably also has a portion in contact with the reinforcement layer. Preferably, the second filamentous member is wound so that those portions of the second filamentous member which are adjacent to each other along the longitudinal direction of the catheter are in contact with each other.

The second filamentous member may be substantially circular or elliptic in cross-sectional shape. The distance between the distal end of the marker and the distal end of the catheter is preferably not more than 1.0 mm, while the overall length of the marker is in the range of 0.5 to 1 mm.

Preferred materials for the marker include gold, platinum, tungsten, or an alloy containing at least one of these metals.

The first filamentous member may be flat in cross-sectional shape and preferably possesses a thickness not more than 80% of the filament diameter of the second filamentous member.

The first filamentous member may be substantially circular in cross-sectional shape. In addition, the first filamentous member and the second filamentous member are preferably wound in the same direction.

Also, the gap between those portions of the first filamentous member which are adjacent to each other along the longitudinal direction of the catheter is preferably 2 to 20 times the filament diameter of the second filamentous member.

The catheter here includes the marker having a portion in close contact with the inner layer, in the gap between the adjacent portions of the first filamentous member constituting the reinforcement layer. Therefore, the outside diameter of the catheter can be set to be relatively small. Thus, this construction is advantageous from the standpoint of reducing the outer diameter of the catheter.

In addition, the marker is spiral in shape and is composed of the second filamentous member having a filament diameter smaller than the gap. Therefore, the catheter possesses excellent flexibility. The safety of the catheter and the performance ability of the catheter to follow a blood vessel are enhanced.

BRIEF DESCRIPTION OF THE DRAWING FIGURES

DETAILED DESCRIPTION

Figure 1:
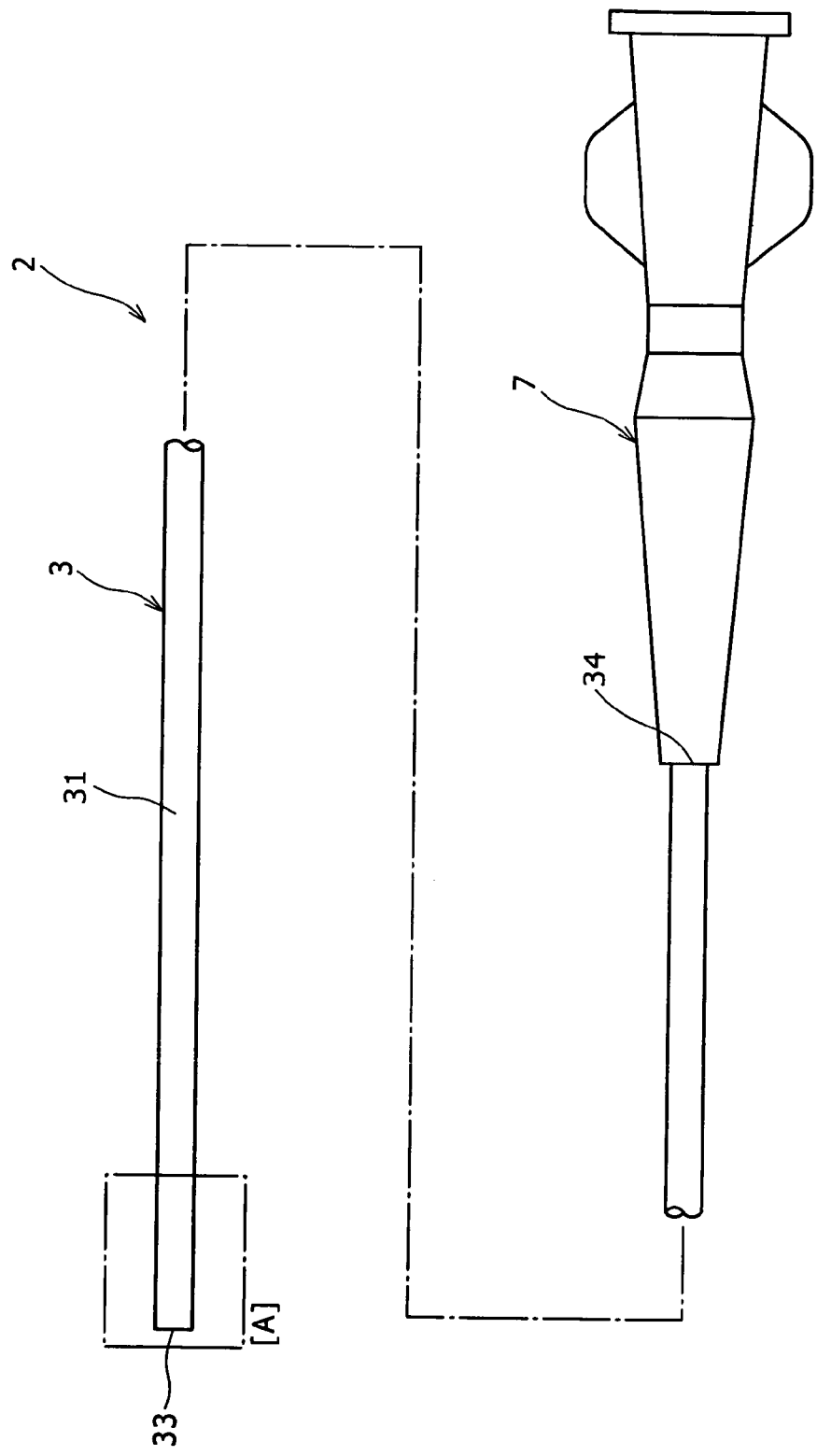
FIG. 1 is an overall view of a first embodiment of a catheter according to the disclosure herein.
Figure 2:
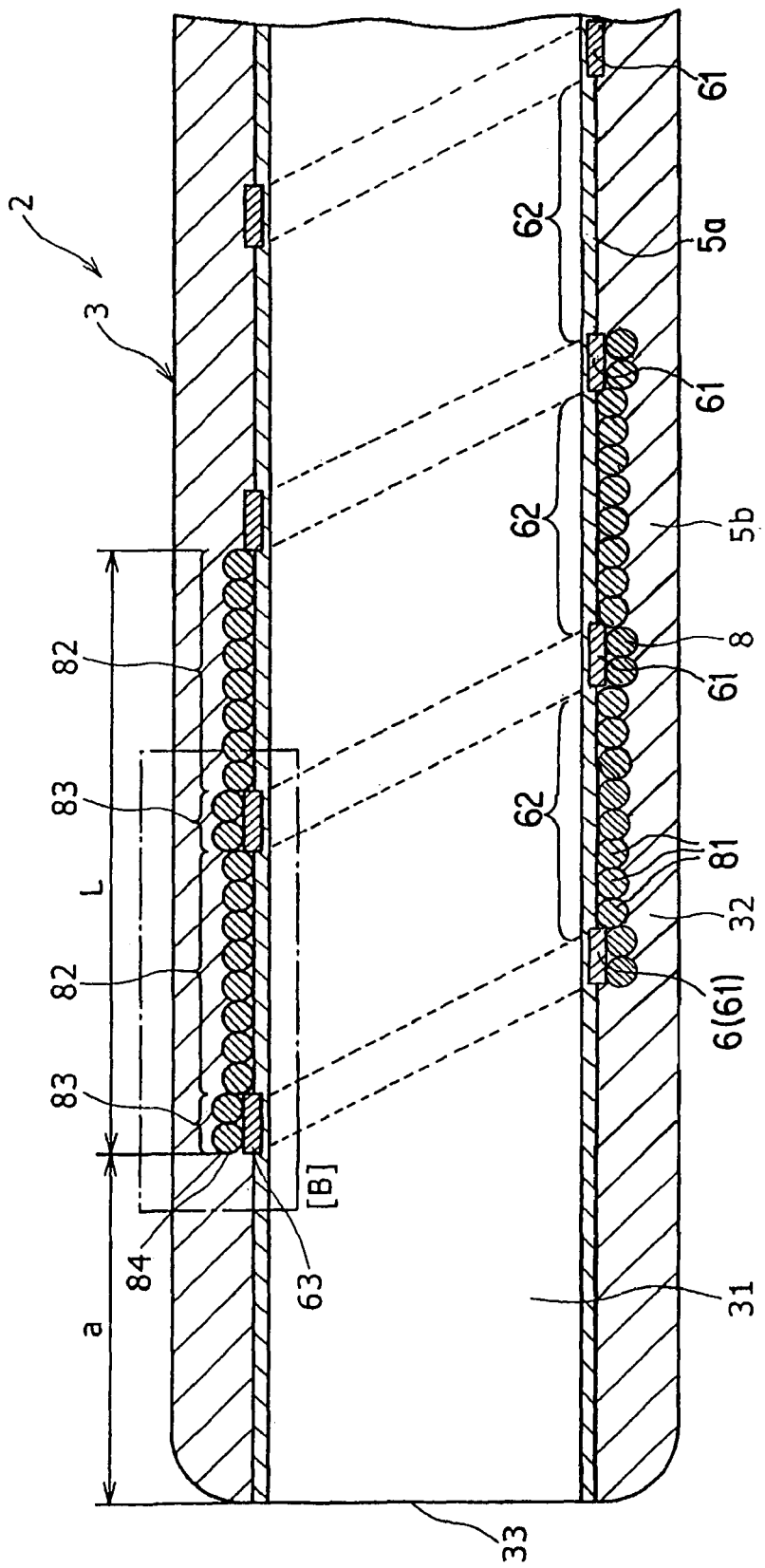
FIG. 2 is an enlarged cross-sectional view of the portion of the catheter identified as [A] in FIG. 1.
Figure 3:
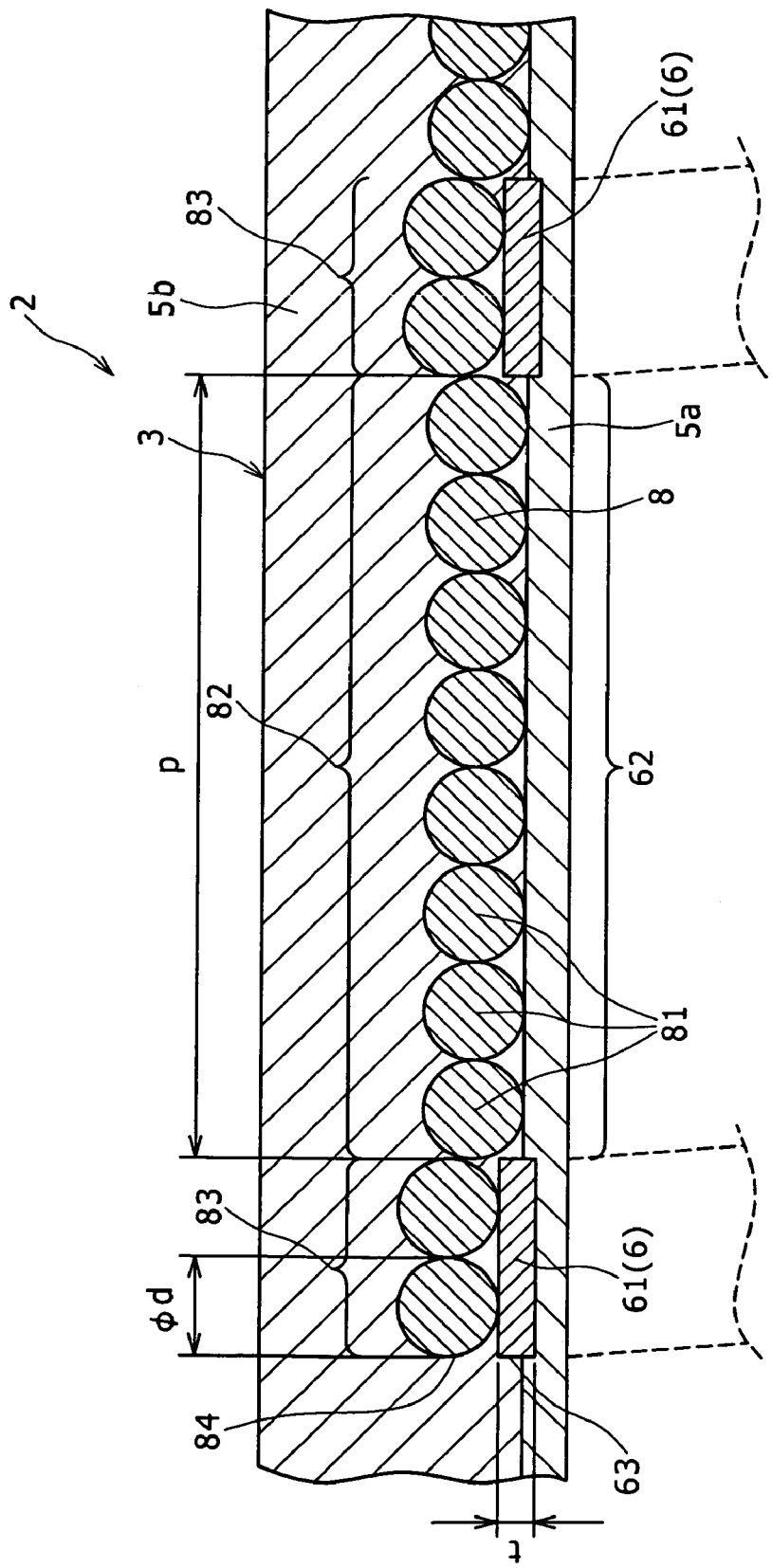
FIG. 3 is an enlarged cross-sectional view of the portion of the catheter identified as [B] FIG. 2.

FIG. 1 is an overall view of a first embodiment of a catheter disclosed herein, while FIGS. 2 and 3 are enlarged cross-sectional views of portions of the catheter. For reference purposes in the description that follows, the right side in FIGS. 1-3 is referred to as the "proximal end (proximal)", and the left side is referred to as the "distal end (distal)".

The catheter 2 shown in FIG. 1 includes a catheter body 3 which is flexible, and a hub 7 attached to the proximal end 34 of the catheter body 3.

A lumen (inner cavity) 31 is provided in the catheter body 3 and extends over the range from the proximal end 34 to the distal end 33 thereof. At the time of inserting the catheter 2 into a blood vessel, a guide wire is passed through the lumen 31. The lumen 31 in the catheter body 3 can also be used as a passage for a contrast medium, a liquid chemical, a cleaning liquid, and the like.

The hub 7 functions as an insertion port for inserting the guide wire into the lumen 31, a feeding port for feeding a contrast medium, a liquid chemical, a cleaning liquid, or the like into the lumen 31, and the like; besides, the hub 7 functions also as a grip portion at the time of operating the catheter 2.

As shown in FIGS. 2 and 3, the catheter body 3 comprises an inner layer 5a, an outer layer 5b, a reinforcement layer 6 located between the inner layer 5a and the outer layer 5b, and a marker 8 formed of a material possessing contrast properties (contrast material).

In the illustrated configuration, the thickness (layer thickness) of the inner layer 5a is less than the thickness of the outer layer 5b.

Examples of material(s) for the inner layer 5a and the outer layer 5b include polyolefins such as polyethylene, polypropylene, ethylene-propylene copolymer, ethylene-vinyl acetate copolymer, crosslinked ethylene-vinyl acetate copolymer, etc., polyvinyl chloride, polyester (PET, PBT, PEN, etc.), polyamides, polyimides, polyurethane, polystyrene, polycarbonates, fluoro-resins (polytetrafluoroethylene, etc.), silicone resins, silicone rubbers, and other various elastomers (for example, polyurethane-based, polyamide-based, polyester-based or the like thermoplastic elastomers). The materials described above can be used individually or in combination. Incidentally, the material(s) constituting the inner layer 5a and the outer layer 5b may be the same as or different from one another.

Where the materials constituting the inner layer 5a and the outer layer 5b are different, materials different in flexibility (rigidity) can be used. For example, in the case of the construction shown in FIG. 2, where the inner layer 5a possesses a smaller thickness than the outer layer 5b, the outer layer 5b may be formed of a material possessing more flexibility than the material of the inner layer 5a. In this way, it is possible to make the catheter body 3, particularly, the distal end portion 32 of the catheter body, rich in flexible.

In addition, the inner layer 5a may be formed of polytetrafluoroethylene, fluorinated ethylene-propylene copolymer (FEP), a high-density polyethylene, or the like material, whereas the outer layer 5b may be formed of a synthetic resin permitting easy fixation of a hydrophilic material to the surface thereof, such as polyurethane elastomer, polyamide elastomer, polyester elastomer, etc. It is thus possible to enhance the slidability of a guide wire in the lumen 31 of the catheter body 3, to enhance the slidability at the time of inserting the catheter into a blood vessel, and to perform the inserting operation more smoothly and assuredly.

While the drawing figures illustrate the thickness of the inner layer 5a being less than the thickness of the outer layer 5b, it is to be understood that the disclosed construction is not limited in this regard. For example, the thickness of the inner layer 5a may be larger than the thickness of the outer layer 5b, or the thickness of the inner layer 5a may be roughly equal to the thickness of the outer layer 5b.

As shown in FIG. 2, the reinforcement layer 6 is disposed (embedded) in the tube wall of the catheter body 3, that is between the inner layer 5a and the outer layer 5b. As a result of this, properties and characteristics of the catheter 2 such as the torque transmission performance, pushability, kink resistance and follow-up performance are enhanced, the operationality at the time of inserting the catheter 2 into a blood vessel is enhanced, and the pressure resistance of the catheter 2 is enhanced when the internal pressure (liquid pressure) inside the lumen 31 is raised.

The reinforcement layer 6 includes a spiral first filamentous member 61, the winding direction of which is counterclockwise as viewed from the distal side of the catheter 2. The reinforcement layer 6 is disposed such that a gap 62 exists between those portions of the first filamentous member 61 which are adjacent to each other along the longitudinal direction of the catheter 2. The reinforcement layer 6 can thus be disposed in a spiral manner or form. The distance (breadth) p of each gap 62 is substantially constant. Thus, portions of the reinforcement layer 6 which are longitudinally adjacent one another are spaced apart from one another in the longitudinal direction.

The cross-sectional shape of the first filamentous member 61 is flat (including generally flattened), for example a rectangle or an ellipse. This makes it possible to restrain or prevent the outside diameter of the catheter body 3 from being undesirably large at the portion of the catheter body 3 where the reinforcement layer 6 (the first filamentous member 61) is provided. This thus helps contribute to a reduction of the outer diameter of the catheter body 3.

The reinforcement layer 6 is meritorious in that the strength of the reinforcement layer 6 can be relatively easily controlled to a desired strength by appropriately selecting characteristics or the arrangement of the reinforcement layer 6 such as the filament material and filament size of the first filamentous member 61, and the arrangement density (dependent on the number of turns in the spiral form, etc.) of the first filamentous member 61.

Examples of the material constituting the first filamentous member 61 include metallic material such as stainless steel, tungsten, piano wire, Ni—Ti alloy, etc., reinforced resin fibers such as Aramide, Kevlar, etc., and carbon fiber.

As shown in FIGS. 2 and 3, the marker 8 having a contrast property, particularly radiopaqueness, is disposed (embedded) at the distal end portion 32 of the catheter body 3. This ensures that the position of the distal end portion 32 of the catheter body 3 in a living body can be confirmed from outside the living body under radioscopic observation.

The marker 8 is composed of a spiral second filamentous member 81. As shown in FIG. 3, the second filamentous member 81 has a filament diameter φd set to be smaller than the distance p (gap 62).

The marker 8 includes an inner layer close contact portion 82 and a reinforcement layer close contact portion 83. The inner layer close contact portion 82 is a site or portion of the marker 8 that is in close contact with the inner layer 5a in the gap 62. That is, the inner layer close contact portion 82 is in contact with the inner layer 5a in the regions between adjacent windings of the spiral filamentous member 61. The reinforcement layer close contact portion 83 is a site or portion of the marker 8 that is in close contact with the reinforcement layer 6.

Since the marker 8 is in close contact with the inner layer 5a and the reinforcement layer 6, the outside diameter of the catheter body 3 can be prevented or restrained from increasing at the distal end portion 32 of the catheter body 3 (i.e., at the portion of the catheter body 3 where the marker 8 is located), thus contributing to a reduction in the outside diameter of the catheter body 3.

In addition, the second filamentous member 81 is wound in such a manner that those portions of the second filamentous member 81 which are adjacent to each other along the longitudinal direction of the catheter 2 are in contact with each other. That is, the second filamentous member 81 is densely wound.

This helps contribute to a construction in which the number of turns of the second filamentous member 81 in the gap 62 is relatively large. That is, the proportion of the inner layer close contact portion 82 in the marker 8 is relatively high. Therefore, the proportion of the three-layer portion, composed of the inner layer 5a, the marker 8 (the inner layer close contact portion 82) and the outer layer 5b, is higher than the proportion of the four-layer portion, composed of the inner layer 5a, the reinforcement layer 6, the marker 8 (the reinforcement layer close contact portion 83) and the outer layer 5b. Thus, the outside diameter of the distal end portion 32 can be assuredly prevented or restrained from increasing. As a result, this configuration contributes to a reduction in the outer diameter of the catheter body 3.

The distance p across the gap 62 (i.e., the distance between adjacent windings of the spiral filamentous member 61) is not particularly limited. However, the distance p is, for example, preferably 2 to 20 times the filament diameter $\phi d$ of the second filamentous member 81, more preferably 4 to 10 times the filament diameter $\phi d$.

If the distance p is less than the lower limit just-mentioned, the area over which the marker 8 and the inner layer 5a are in close contact with each other is so small (i.e., the proportion of the inner layer close contact portion 82 in the marker 8 is quite low) that it may be difficult to avoid or prevent the outside diameter of the distal end portion 32 from increasing. Therefore, it may be difficult to reduce the diameter of the catheter body 3 to the extent desired. On the other hand, if the distance p exceeds the upper limit just-mentioned, the gap 62 is so large (broad) that the reinforcing effect of the reinforcement layer 6 may be reduced.

Since the second filamentous member 81 is densely wound as above-mentioned, it is relatively easy to confirm the position of the distal end portion 32 of the catheter body 3 under radioscopic observation. That is, under radioscopic observation, the marker 8 (the second filamentous member 81) can be relatively easily observed.

In addition, the second filamentous member 81 is substantially circular in cross-sectional shape. This helps facilitate easy bending of the marker 8 and, therefore, can provide the catheter 2 (the catheter body 3) with excellent flexibility.

The thickness t of the first filamentous member 61 is not particularly limited. Preferably, the thickness t is, for example, not more than 80%, more preferably in the range of 20 to 50%, of the filament diameter $\phi d$ of the second filamentous member 81.

When the thickness t is in the range just-mentioned, the proportion of the layer thickness of the reinforcement layer 6 in the four-layer portion can be set to be relatively low. This advantageously contributes to a reduction of the outer diameter of the catheter body 3.

In addition, the distance "a" between the distal end 84 of the marker 8 and the distal end 33 of the catheter 2 is not particularly limited. By way of example, the distance "a" is preferably not more than 1 mm, more preferably in the range of 0.5 to 1 mm. When the distance "a" is within this range, the position of the vicinity of the distal end 33 of the catheter 2 in a living body can be reliably confirmed under radioscopic observation.

In addition, while the overall length L of the marker 8 (i.e., the distance between the distal-most end of the marker and the proximal-most end of the marker as measured along the longitudinal direction of the catheter body) is not particularly limited; as an example, the overall length L is preferably in the range of 0.5 to 1 mm, more preferably 0.7 to 1 mm.

When the overall length L is within the such range, the position of the vicinity of the distal end 33 of the catheter 2 can be confirmed in a more reliable manner under radioscopic observation.

In addition, the winding direction of the second filamentous member 81 is preferably the same as the winding direction of the first filamentous member 61. This helps facilitate favorable bending of the catheter 2.

The marker 8 is composed, for example, of one of various metallic materials including stainless steel, super-elastic alloys, cobalt alloys, noble metals such as gold, platinum, tungsten, etc. and alloys containing these metals. Where the marker 8 is composed of a radiopaque material such as noble metal, the marker 8 itself has a radioscopic contrast property and so the catheter 2 can be inserted into a living body while reliably confirming the position of the distal end portion 32 of the catheter 2 under radioscopic observation.

In the catheter 2 constructed as described above, the marker 8 is in close contact with the inner layer 5a and the reinforcement layer 6 and so the outside diameter of the catheter body 3 can be set to be relatively small. This contributes to reducing the outer diameter of the catheter body 3. Since the diameter of the catheter body 3 is thus reduced, the catheter body 3 can be relatively easily passed through a portion of small inside diameter, such as a stenosis portion and a peripheral portion, of a blood vessel.

In addition, since the marker 8 and the reinforcement layer 6 are each composed of spiral filamentous members, the distal end portion 32 of the catheter body 3 is relatively easily bent, i.e., can be made fairly flexible.

The marker 8 may be composed of a material having a contrast property, to permit confirmation of its position, using imaging methods other than radioscopy, such as CT scan, MRI, etc.

The cross-sectional shape of the second filamentous member 81 is not limited to a substantially circular shape. For example, an elliptical shape may be adopted as the cross-sectional shape of the second filamentous member 81.

The method of manufacturing the catheter body 3 is not particularly limited. Set forth below is a description of an example of one method that can be employed.

[1] First, the inner layer 5a is moved at a constant velocity in the distal direction (in the direction of one end) while rotating it, and the first filamentous member 61 (the reinforcement layer 6) is wound so as to produce a predetermined distance p between adjacent windings. In this way, the reinforcement layer 6 is provided on the surface of the inner layer 5a.

[2] Next, the body obtained in the preceding step [1] is moved in the distal direction (in the direction of one end) at a velocity lower than that in preceding step [1] while rotating it, and the second filamentous member 81 is wound in a dense pattern. This results in the marker 8 being in close contact with the inner layer 5a and the reinforcement layer 6.

[3] Subsequently, the outer layer 5b is fitted over the body obtained in the preceding step [2], and the components are united, for example by heating, whereby the catheter body 3 is manufactured. In this case, a heat-shrinkable tube may be used as the outer layer 5b. In addition, either one of the inner layer 5a and the outer layer 5b may be a coating film formed by a coating method, for example, coating, dipping, spraying, or the like.

In step [2], the second filamentous member 81 is wound while applying a tension to the second filamentous member 81 in the elastic deformation region of the second filamentous member. This ensures that, even when the catheter body 3 as a whole is bent, the second filamentous member 81 (the marker 8) is not put into plastic deformation (i.e., is not plastically deformed). Therefore, the second filamentous member 81 returns to the densely wound state, and is kept in close contact with the inner layer 5a and the reinforcement layer 6.

In addition, it is preferable that a coating layer composed of a material capable of easily lowering or reducing friction (hereinafter referred to as "low-friction material") is formed on the outer surface (at least the surface of the distal end portion 32) of the catheter body 3. This helps facilitate and enhance the slidability of the catheter body 3 at the time of insertion of the catheter body 3 into a blood vessel. Particularly, the catheter body 3 can be smoothly passed through an angiostenosis.

Examples of the low-friction material include hydrophilic materials and hydrophobic materials. Among these materials, hydrophilic materials are preferred.

Examples of the hydrophilic materials (hydrophilic polymers) include cellulose polymeric materials, polyethylene oxide polymeric materials, maleic anhydride polymeric materials (e.g., maleic anhydride copolymers such as methyl vinyl ether-maleic anhydride copolymer), acrylamide polymeric materials (e.g., polyacrylamide, polyglycidyl methacrylate-dimethyl acrylamide (PGMA-DMAA) block copolymer), water-soluble nylon, polyvinyl alcohol, and polyvinyl pyrrolidone.

In many cases, such hydrophilic materials display lubricity through wetting (water absorption), thereby lowering the frictional resistance (sliding resistance) between the catheter body 3 and the inside wall of a blood vessel. As a result, at the time of inserting the catheter body 3 into a blood vessel, the slidability of the catheter body 3 is enhanced, and the operational ability of the catheter is improved.

The layer of hydrophilic material (or hydrophobic material) as described above is provided on the outer surface of at least the distal end portion 32 of the catheter body 3, or may be provided on the outer surface over the entire length of the catheter body 3.

The coating layer as described above can be formed by a coating method, for example, coating, dipping, spraying, or the like.

Figure 4:
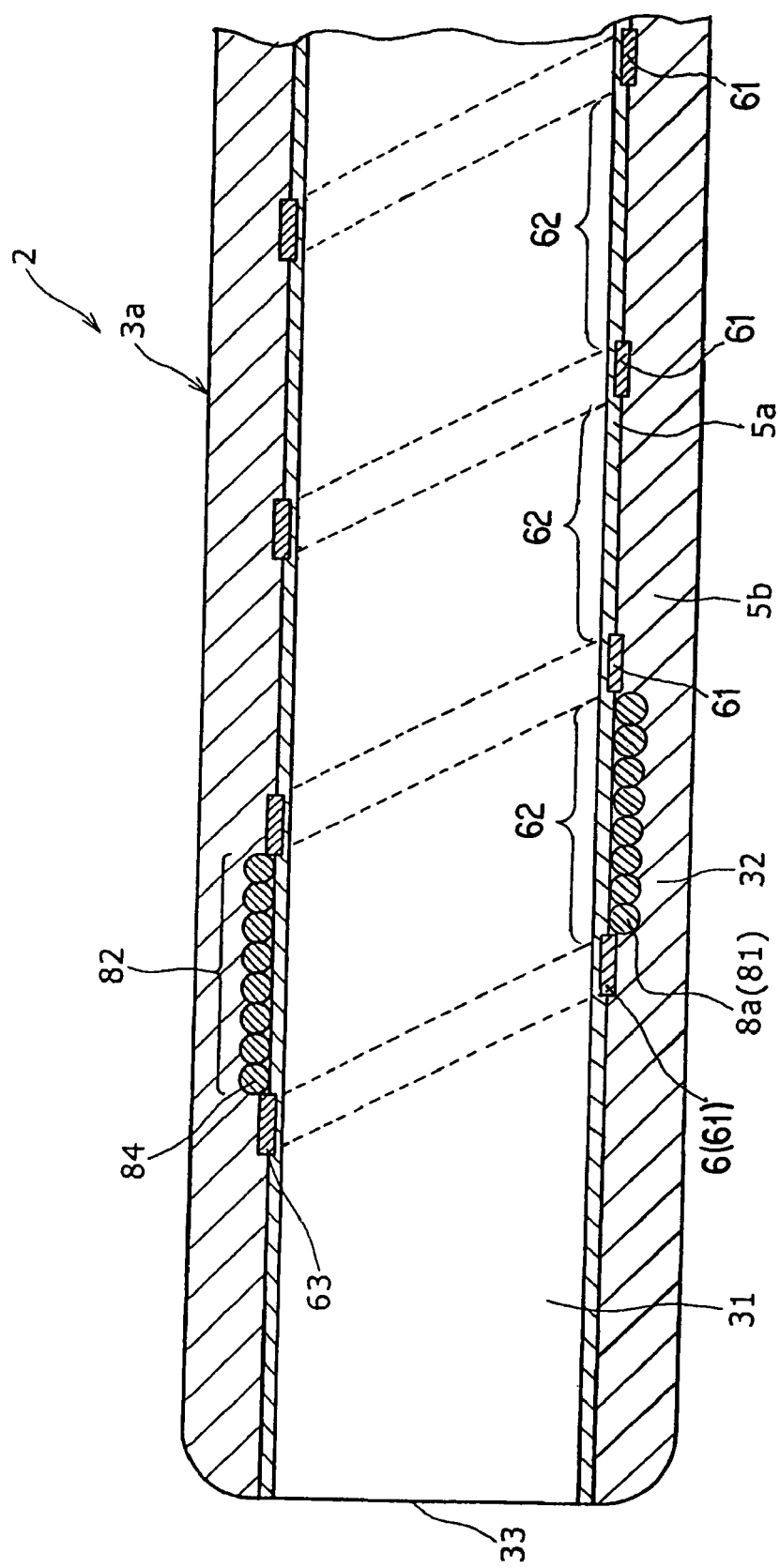
FIG. 4 is a cross-sectional view of a portion of a catheter according to a second embodiment in the vicinity of the distal end portion of the catheter.

Referring to FIG. 4, a second embodiment of the catheter will be described. FIG. 4 is a cross-sectional view showing a portion of the catheter in the vicinity of the distal end portion of the catheter. For convenience of description, the right side in FIG. 4 is referred to as the "proximal end (proximal)" and the left side is referred to as the "distal end (distal)".

The following description of the second embodiment of the catheter will primarily describe the catheter from the standpoint of differences relative to the above-described first embodiment. A detailed description of features which are common to both embodiments is not repeated.

This second embodiment of the catheter is the same as the above-described first embodiment, except for the configuration of the marker. The catheter body 3a shown in FIG. 4 includes a marker 8a, but the marker 8a in this second embodiment lacks a reinforcement layer close contact portion 83. That is, unlike the marker 8 in the first embodiment, the marker 8a in the second embodiment has the only inner layer close contact portion 82 which is in close contact with the inner layer 5a. Thus, the marker 8a is only in close contact with the inner layer 5a.

The catheter body 3a according to this second embodiment thus differs from the first embodiment in that the catheter body 3a lacks the four-layer portion composed of the inner layer 5a, the reinforcement layer 6, the marker 8, and the outer layer 5b. Therefore, it is possible to further prevent or restrain the outside diameter of the distal end portion 32 of the catheter body 3 from increasing. This advantageously contributes to a reduction of the diameter of the catheter 2.

While the marker 8a is illustrated as being provided in one gap 62 between adjacent windings of the reinforcement layer 6, the catheter construction is not limited in this regard. For example, the marker 8a may be provided in each of a plurality of gaps 62. Further, the marker 8a may be provided between the distal end 33 of the catheter body 3 and the distal end 63 of the reinforcement layer 6.

Although embodiments of the present invention have been described with reference to the drawing figures, the catheter of the present invention is not limited in this regard. Each component constituting the catheter can be replaced by any other arbitrary components providing similar functions. In addition or alternatively, components can be added thereto.

While each of the inner layer and the outer layer is uniform in thickness over the whole length of the catheter body in the illustrated embodiments, the catheter is not limited in this regard. For instance, the thickness of one or both layers may be gradually reduced along the distal direction at the distal portion of the catheter body.

While the first filamentous member constituting the reinforcement layer is described as being wound counterclockwise in the illustrated versions, it is to be recognized that the first filamentous member may be wound clockwise.

The drawing figures illustrate the gaps 62 being substantially constant with respect to the distance p, it is also possible that the distance p may be gradually increased along the distal direction. Where the distance p is gradually increased along the distal direction, the degree (effect) of reinforcement can be gradually reduced along the distal direction. As a result, a distal end portion 32 of the catheter 2 can be provided with favorable flexibility.

In addition, the cross-sectional shape of the first filamentous member is not limited to the flat shape illustrated. For example, the cross-sectional shape may be any of several other shapes such as a substantially circular shape. Where the first filamentous member is substantially circular in cross-sectional shape, the kink resistance is meritoriously enhanced.

The winding direction of the second filamentous member constituting the marker is not limited to the same direction as that of the first filamentous member, and may be a different direction, namely a direction reverse to that of the first filamentous member.

It is also to be recognized that the marker may be adhered to (in close contact with) the inner layer and/or the reinforcement layer through an adhesive layer.

The principles, preferred embodiments and mode of operation have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A catheter positionable in a living body comprising:
a catheter body possessing a lumen, the catheter body comprising:
an inner layer extending along at least a distal end portion of the catheter body, the inner layer possessing an inner surface exposed to the lumen of the catheter body;
an outer layer contacting the inner layer and extending along at least the distal end portion of the catheter body;
a reinforcement layer between the inner layer and the outer layer;
the reinforcement layer possessing a radially outwardly facing outer surface;
the reinforcement layer comprising a first filamentous member, the first filamentous member extending in a spiral manner about the inner layer so that portions of the first filamentous member which are adjacent one another in a longitudinal direction of the catheter body are spaced apart;
a marker comprised of a material possessing contrast properties permitting confirmation of a position of the distal end portion of the catheter from outside the living body;
the marker comprising a second filamentous member comprised of the material possessing contrast properties, the second filamentous member extending in a spiral manner about the inner layer and having a distal end and a proximal end;
a majority of the second filamentous member being positioned between portions of the first filamentous member which are adjacent one another in the longitudinal direction of the catheter body and being an inner layer close contact portion which is in direct contact with the inner layer;
the majority of the second filamentous member positioned between the portions of the first filamentous member including three or more adjacent spiral windings which contact each other between the portions;
a remainder of the second filamentous member, comprising at least a portion of the second filamentous member, directly overlying the radially outwardly facing outer surface of the reinforcement layer;
the marker and the reinforcement layer being covered by the outer layer;
wherein all portions of the second filamentous member which are adjacent to each other along the longitudinal direction of the catheter body are in contact with each other; and
wherein the first filamentous member extends proximally beyond the proximal end of the second filamentous member in the longitudinal direction of the catheter body, and the inner layer close contact portion which is in direct contact with the inner layer is disposed only at the distal end portion of the catheter body.

2. The catheter as set forth in claim 1, wherein a distance between a distal-most end of the marker and a distal-most end of the catheter body is not more than 1 mm.

3. The catheter as set forth in claim 1, wherein a distance between a distal-most end of the marker and a proximal-most end of the marker as measured along the longitudinal direction of the catheter body is 0.5 mm to 1.0 mm.

4. The catheter as set forth in claim 1, wherein the first filamentous member possesses a flat cross-sectional shape.

5. The catheter as set forth in claim 4, wherein the second filamentous member possesses a filament diameter, the first filamentous member possessing a thickness not more than 80% of the filament diameter of the second filamentous member.

6. The catheter as set forth in claim 1, wherein the entirety of the first filamentous member is wound in one direction, and the entirety of the second filamentous member is also wound in the one direction.

7. A catheter positionable in a living body comprising:
an inner layer;
an outer layer;
a reinforcement layer located between the inner layer and the outer layer;
a marker comprised of a contrast material permitting confirmation of a position of a distal end portion of the catheter from outside the living body;
the reinforcement layer comprising a spiral first filamentous member, with a gap between portions of the first filamentous member which are adjacent to each other along a longitudinal direction of the catheter;
the reinforcement layer possessing a radially outwardly facing outer surface;
the marker comprising a spirally wound second filamentous member comprising the contrast material and possessing a filament diameter smaller than the gap, the spirally wound second filamentous member having a distal end and a proximal end;
a majority of the spirally wound second filamentous member being an inner layer close contact portion which is in direct contact with the inner layer in the gap and including three or more adjacent spiral windings which contact each other in the gap;
a remainder of the spirally wound second filamentous member, comprising at least a portion of the spirally wound second filamentous member, directly overlying the radially outwardly facing outer surface of the reinforcement layer;
wherein all portions of the spirally wound second filamentous member which are adjacent to each other along the longitudinal direction of the catheter are in contact with each other; and
wherein the spiral first filamentous member extends proximally beyond the proximal end of the spirally wound second filamentous member in the longitudinal direction of the catheter, and the inner layer close contact portion which is in direct contact with the inner layer is disposed only at the distal end portion of the catheter.

8. The catheter as set forth in claim 7, wherein the second filamentous member possesses a substantially circular cross-sectional shape.

9. The catheter as set forth in claim 7, wherein a distance between a distal-most end of the marker and a distal-most end of the catheter is not more than 1 mm.

10. The catheter as set forth in claim 7, wherein a distance between a distal-most end of the marker and a proximal-most end of the marker as measured along the longitudinal direction of the catheter is 0.5 mm to 1.0 mm.

11. The catheter as set forth in claim 7, wherein the marker is made of gold, platinum, tungsten, or an alloy containing at least one of gold, platinum and tungsten.

12. The catheter as set forth in claim 7, wherein the first filamentous member possesses a flat cross-sectional shape.

13. The catheter as set forth in claim 12, wherein a thickness of the first filamentous member is not more than 80% of the filament diameter of the second filamentous member.

14. The catheter as set forth in claim 7, wherein the first filamentous member possesses a substantially circular cross-sectional shape.

15. The catheter as set forth in claim 7, wherein the first filamentous member and the second filamentous member are wound in the same direction.

16. The catheter as set forth in claim 7, wherein the gap is 2 to 20 times the filament diameter of the second filamentous member.

17. A catheter positionable in a living body comprising:
a catheter body possessing a lumen, the catheter body comprising:
an inner layer extending along at least a distal end portion of the catheter body, the inner layer possessing an inner surface exposed to the lumen of the catheter body;
an outer layer contacting the inner layer and extending along at least the distal end portion of the catheter body;
a reinforcement layer between the inner layer and the outer layer;
the reinforcement layer possessing a radially outwardly facing outer surface
the reinforcement layer comprising a first filamentous member, the first filamentous member extending in a spiral manner about the inner layer so that portions of the first filamentous member which are adjacent one another in a longitudinal direction of the catheter body are spaced apart;
a marker comprised of a material possessing contrast properties permitting confirmation of a position of the distal end portion of the catheter from outside the living body;
the marker comprising a second filamentous member comprised of the material possessing contrast properties, the second filamentous member extending in a spiral manner about the inner layer and having a distal end and a proximal end;
a majority of the second filamentous member being an inner layer close contact portion which is in direct contact with the inner layer and which is positioned between portions of the first filamentous member which are adjacent one another in the longitudinal direction of the catheter body, the inner layer close contact portion which is in direct contact with the inner layer being comprised of three or more adjacently positioned spiral windings of the second filamentous member which contact each other between the portions;
a remainder of the second filamentous member, comprising at least a portion of the second filamentous member, being a reinforcement layer close contact portion which directly overlies the radially outwardly facing outer surface of the reinforcement layer;
the marker and the reinforcement layer being covered by the outer layer;
wherein all portions of the second filamentous member which are adjacent to each other along the longitudinal direction of the catheter body are in direct contact with each other; and
wherein the first filamentous member extends proximally beyond the proximal end of the second filamentous member in the longitudinal direction of the catheter body, and the inner layer close contact portion which is in direct contact with the inner layer is disposed only at the distal end portion of the catheter body.

18. A catheter positionable in a living body comprising:
a catheter body possessing a lumen, the catheter body comprising:
an inner layer extending along at least a distal end portion of the catheter body, the inner layer possessing an inner surface exposed to the lumen of the catheter body;
an outer layer contacting the inner layer and extending along at least the distal end portion of the catheter body;
a reinforcement layer between the inner layer and the outer layer;
the reinforcement layer possessing a radially outwardly facing outer surface;
the reinforcement layer comprising a first filamentous member, the first filamentous member extending in a spiral manner about the inner layer so that spiral windings of the first filamentous member do not contact one another and so that a space exists between spiral windings of the first filamentous member which are adjacent one another in a longitudinal direction of the catheter body;
a marker comprised of a material possessing contrast properties permitting confirmation of a position of the distal end portion of the catheter from outside the living body;
the marker comprising a second filamentous member comprised of the material possessing contrast properties, the second filamentous member extending in a spiral manner about the inner layer and having a distal end and a proximal end;
the first filamentous member extending spirally in a winding direction, the second filamentous member extending spirally in a winding direction that is the same as the winding direction of the first filamentous member;
a majority of the second filamentous member being an inner layer close contact portion which is in direct contact with the inner layer;
a remainder of the second filamentous member, comprising at least a portion of the second filamentous member, being a reinforcement layer close contact portion which directly overlies the radially outwardly facing outer surface of the reinforcement layer;
the inner layer close contact portion which is in direct contact with the inner layer being comprised of a first group of at least three spiral windings positioned so that the spiral windings of the first group which are adjacent each other in the longitudinal direction of the catheter body are in contact with one another, and a second group of at least three spiral windings positioned so that the spiral windings of the second group which are adjacent each other in the longitudinal direction of the catheter body are in contact with one another;
the first group of at least three spiral windings being positioned between first and second windings of the first filamentous member which are adjacent one another in the longitudinal direction of the catheter body, the second group of at least three spiral windings being positioned between the second winding and a third winding of the first filamentous member which are adjacent one another in the longitudinal direction of the catheter body;
the outer layer covering and in contact with the marker and the reinforcement layer; and
wherein the first filamentous member extends proximally beyond the proximal end of the second filamentous member in the longitudinal direction of the catheter body, and the inner layer close contact portion which is in direct contact with the inner layer is disposed only at the distal end portion.

* * * * *